(12) United States Patent
Schwalm et al.

(10) Patent No.: US 6,562,464 B1
(45) Date of Patent: May 13, 2003

(54) UTILIZATION OF PHENYLGLYOXALIC ACID ESTERS AS PHOTOINITIATORS

(75) Inventors: Reinhold Schwalm, Wachenheim (DE); Rainer Königer, Freinsheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/926,194

(22) PCT Filed: Mar. 23, 2000

(86) PCT No.: PCT/EP00/02609

§ 371 (c)(1),
(2), (4) Date: Sep. 21, 2001

(87) PCT Pub. No.: WO00/56822

PCT Pub. Date: Sep. 28, 2000

(30) Foreign Application Priority Data

Mar. 24, 1999 (DE) .......................................... 199 13 353

(51) Int. Cl.$^7$ ................................................. B32B 9/04
(52) U.S. Cl. ................. 428/411.1; 427/372.1; 427/375; 427/384; 427/487; 427/508; 427/517; 427/519; 427/521; 427/553; 427/558; 430/56; 430/270.1; 430/581.1; 522/1; 522/6; 522/8; 522/9; 522/37; 549/465
(58) Field of Search ................................. 427/553, 487, 427/508, 517, 519, 521, 558, 372.2, 375, 384; 430/56, 270.1, 581.1; 522/1, 6, 8, 9, 37; 549/465; 428/411.1

(56) References Cited

U.S. PATENT DOCUMENTS

| 4,024,297 A | 5/1977 | Gruber |
| 4,038,164 A | 7/1977 | Via |
| 4,138,299 A | 2/1979 | Bolgiano |
| 4,173,682 A | 11/1979 | Noomen et al. |
| 4,279,718 A | 7/1981 | Schuster et al. |
| 4,279,720 A | 7/1981 | Berner |
| 4,308,394 A | 12/1981 | Schuster et al. |
| 4,415,604 A | 11/1983 | Nativi |
| 5,234,970 A | 8/1993 | Kyle |
| 5,484,850 A | 1/1996 | Kempter et al. |
| 5,639,560 A | 6/1997 | Moens et al. |
| 5,703,198 A | 12/1997 | Twigt et al. |
| 6,005,017 A | 12/1999 | Daly et al. |
| 6,017,640 A | 1/2000 | Muthiah et al. |
| 6,048,660 A * | 4/2000 | Leppard et al. .......... 430/270.1 |

FOREIGN PATENT DOCUMENTS

| EP | 650 985 | 5/1995 |
| EP | 965 621 | 12/1999 |
| WO | WO 98/33761 | 8/1998 |

OTHER PUBLICATIONS

W. Reich, et al., RADTECH '98, Conference Proceedings, pp. 258–265, "Water–Based Radiation–Curable Systems—Newest Investigations", Apr. 19–22, 1998.

Daniel Maetens, RADTECH '98, Conference Proceedings, pp. 170–176, "UV–Powders: Eldorado or Industrial Curiosity?", Apr. 19–22, 1998.

PPCJ, Exhibition Previews, vol. 187, No. 9, pp. 18 and 20, "European Coating Show On Familiar Ground", 1997 (No month avail).

S. Hu, et al., Macromolecules, vol. 31, pp. 322–327, "Photochemically Active Polymers Containing Pendant Ethyl Phenyglyoxylate," 1998 (No month avail.).

\* cited by examiner

*Primary Examiner*—Bernard Pianalto
(74) *Attorney, Agent, or Firm*—Oblon, Spivak, McClelland, Maier & Neustadt, P.C.

(57) ABSTRACT

The use of phenylglyoxalic esters of the formula I

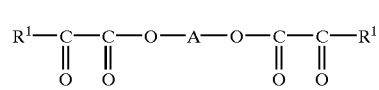

in which the two radicals $R^1$ and A are as defined in the description as photoinitiators in powder coating materials for exterior applications. The compounds of the formula I show little propensity toward yellowing.

12 Claims, No Drawings

UTILIZATION OF PHENYLGLYOXALIC ACID ESTERS AS PHOTOINITIATORS

The present invention relates to the use of certain phenylglyoxalic esters as photoinitiators in powder coating materials for exterior applications.

Conventional radiation-curable coating materials generally include reactive monomers for adjusting the application viscosity (reactive diluents) and are cured at room temperature. These coating materials have the disadvantage that the monomers used as reactive diluents are able to penetrate into porous substrates, such as wood or paper, thereby escaping the UV cure. Furthermore, the exposure of three-dimensional objects may give rise to the incidence of shadow regions, which are insufficiently exposed, meaning that liquid coating materials may remain tacky in these regions. Aqueous UV coating materials have therefore been developed which are heat treated for drying and are cured at relatively high temperatures, see W. Reich et al., RadTech 98, Conference Proceedings, Chicago 1998, 258–265.

In order to avoid the abovementioned problems, furthermore, UV-curable powder coating materials have been proposed which are applied to the substrate by conventional methods and then melted and cured at relatively high temperatures; see, for example, RadTech, Conference Proceedings, Chicago 1998, 170–176; JOT 1998, 2, 44–47; PPCJ 1997, (9), 18,20; EP 636 669 A; 650 985 A; 650 978 A and U.S. Pat. No. 5,639,560. Also known are Dual Cure Systems where curing takes place by means of radiation and atmospheric humidity (U.S. Pat. No. 4,138,299; 4,173,682; 4,415,604 and EP 549 116 A) or which comprise a heat-activatable initiator as well as a UV free-radical initiator (EP 844 286 A).

It has been found that, under the thermal stress of the melting of powder coating materials, many of the common photoinitiators are too volatile to permit curing by UV irradiation. Furthermore, the depletion of photoinitiators at the surface of the coating material is particularly undesirable, since it is there that there is the greatest oxygen inhibition, so resulting in inadequate curing and thus poor film properties, such as low chemical resistance and inadequate blocking resistance. Consideration has therefore been given to the less volatile arylglyoxalic esters as photoinitiators; see, for example, DE 26 39 742 A, U.S. Pat. No. 4,024,297 and DE 198 26 712 A, which latter application has a priority date earlier but a publication date later than the present specification. Polymer-bound arylglyoxalates are known from DE 28 25 955 A and Macromolecules 1998, 31, 322–327.

WO 98/33761 describes diesters of arylglyoxalic acids with diols. These esters are low-volatility photoinitiators which are used in liquid systems. The possibility of their use in powder coating materials is only mentioned in general terms.

It is an object of the present invention to provide improved photoinitiators for use in powder coating materials for exterior applications.

We have found that this object is achieved by certain esters of arylglyoxalic acids with diols, which are particularly suitable as photoinitiators in powder coating materials for exterior applications. In particular it has been found that the esters used in accordance with the invention can be exposed to heat without disadvantage prior to irradiation. We have also found that the photoinitiators exhibit particularly low yellowing levels.

The present invention therefore provides for the use of phenylglyoxalic esters of the formula I

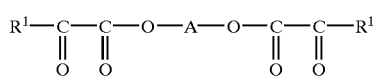

in which the two radicals $R^1$ independently of one another are a radical of the formula

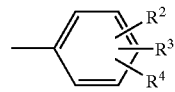

$R^2$, $R^3$ and $R^4$ independently of one another are H, $C_1$–$C_6$-alkyl, which is unsubstituted or substituted by OH, $OC_1$–$C_6$-alkyl or $OCOC_1$–$C_6$-alkyl, or are OH or $OC_1$–$C_6$-alkyl;

A is $C_2$–$C_6$-alkylene or a radical of the formulae

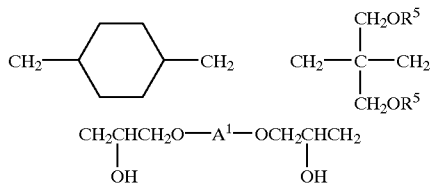

the radicals $R^5$ independently of one another are H or $COCOR^1$, and $A^1$ is $C_2$–$C_6$-alkylene or

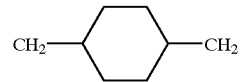

as photoinitiators in powder coating materials for exterior applications.

$C_1$–$C_6$-alkyl is a straight-chain or branched alkyl group having 1 to 6 carbon atoms, preferably 1 to 4 carbon atoms. Examples of alkyl groups are methyl, ethyl, propyl, isopropyl, n-butyl, sec-butyl, isobutyl, tert-butyl, pentyl and hexyl.

$C_2$–$C_6$-alkylene is a straight-chain or branched alkylene group having 2 to 6 carbon atoms. Examples of alkylene groups are methylene, ethylene, propylene, isopropylene, n-butylene, sec-butylene, isobutylene, tert-butylene, pentylene and hexylene.

Preferably, one of the radicals $R^2$, $R^3$ and $R^4$ is $C_1$–$C_6$-alkyl and the other two are H, and with particular preference $R^2$, $R^3$ and $R^4$ are all H.

A is preferably

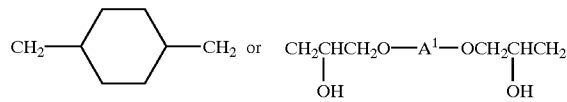

$A^1$ being

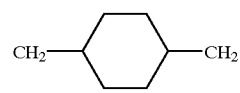

The compounds of the formula I in which A has the preferred definitions indicated are likewise provided by the invention.

The compounds of the formula I are either known or can be prepared by the methods described in WO 98/33761. Furthermore, it is possible to react the desired arylglyoxalic acid with the alcohol in the presence of an acidic catalyst, such as sulfuric acid, p-toluenesulfonic acid, in the manner of a conventional esterification to give the desired ester. The esterification is judiciously conducted in a water-immiscible solvent, for example a hydrocarbon, such as methylcyclohexane, toluene, xylene, etc. The water formed is removed from the reaction mixture in a conventional manner.

The compounds of the formula I in which A is

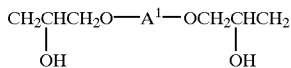

can be prepared by reacting the corresponding arylglyoxalic acid with a diglycidyl ether of the formula

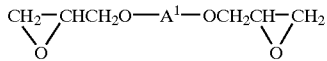

in which $A^1$ is as defined above. The reaction is generally conducted without solvents and in the presence of an appropriate catalyst, such as a tetraalkylammonium halide. The reaction temperature is generally in the range from 80 to 120° C.

The compounds of the formula I can be used as photoinitiators for the photopolymerization of ethylenically unsaturated compounds. In particular, they are suitable as photoinitiators in powder coating materials for interior and, preferably, exterior applications. They can be used alone or together with other photoinitiators. Examples of photoinitiators with which they can be used in a mixture are mono- or bisacylphosphine oxides, benzophenones and hydroxyacetophenones. Further cophotoinitiators are described, for example, in WO 98/33761.

The compounds of the formula I are generally used in radiation-curable compositions. These compositions include at least one ethylenically unsaturated, radiation-curable substance and at least one photoinitiator compound of the formula I, together if desired with further photoinitiators and/or additives. The amount of compounds of the formula I in the compositions is generally in the range from 0.1 to 10% by weight, preferably from 0.5 to 8% by weight, based on the weight of the radiation-curable substance. Where mixtures with other photoinitiators are used, said mixtures generally contain from 0.1 to 50% by weight of said other photoinitiators, based on the overall weight of the mixture.

The amount of radiation-curable substance in the compositions is generally in the range from 10 to 90% by weight, preferably from to 90% by weight, based on the overall weight of the composition. In the case of powder coating materials, the amount of radiation-curable substances is generally in the range from 50 to 90% by weight, preferably from 60 to 90% by weight, based on the overall weight of the composition.

The radiation-curable substance can comprise one or more olefinic, free-radically polymerizable double bonds and be monomeric or polymeric, especially oligomeric, in nature. Examples of monomeric substances (reactive diluents) having a double bond are alkyl or hydroxyalkyl acrylates or methacrylates, such as methyl, ethyl, n-butyl and 2-ethylhexyl acrylate or methacrylate, and 2-hydroxyethyl acrylate or methacrylate. Further examples are (meth)acrylonitrile, (meth)acrylamide, N-$C_1$–$C_4$-alkyl substituted (meth)acrylamides, vinyl esters, such as vinyl acetate, vinyl ethers, such as isobutyl vinyl ether, vinylaromatic compounds, such as styrene, N-vinylpyrrolidone, vinyl chloride and vinylidene chloride.

Examples of monomers having two or more double bonds are the esters of acrylic or methacrylic acid with polyalcohols having preferably 2 to 6 OH groups, such as ethylene glycol, propylene glycol and their counterparts with higher degrees of condensation, such as diethylene glycol, triethylene glycol, dipropylene glycol, tripropylene glycol etc., butanediol, pentanediol, hexanediol, neopentyl glycol, bisphenol A, cyclohexane dimethanol, alcohols with a functionality of three or more, such as glycerol, trimethylolpropane, butanetriol, trimethylolethane, pentaerythritol, dimethylolpropane, dipentaerythritol, sorbitol, mannitol and the corresponding alkoxylated, especially ethoxylated and propoxylated alcohols, and also vinyl acrylate, divinyl benzene, diallyl phthalate, etc.

The oligomeric and/or polymeric radiation-curable substances (radiation-curable binders) are, in particular, polyurethanes, polyesters, polyethers or epoxy resins having ethylenically unsaturated double bonds. Preference is given to polyester acrylates, polyether acrylates and, in particular, polyurethane acrylates (the expression "acrylates" also being intended to embrace the corresponding methacrylates), i.e., esters of acrylic or methacrylic acid with polyesterols, polyetherols and polyurethanes having free hydroxyl groups.

Preferred polyester acrylates are synthesized from saturated or unsaturated polycarboxylic acids, such as succinic acid, adipic acid, phthalic acid, maleic acid, etc., and the abovementioned polyalcohols having preferably 2 to 5 OH groups. The polyester acrylates preferably have a number-average molecular weight in the range from 350 to 10,000, determined by means of gel permeation chromatography (GPC).

The polyether acrylates are synthesized from the abovementioned polyalcohols and preferably have a number-average molecular weight in the range from 350 to 10,000, determined by means of GPC.

Urethane acrylates are obtainable by reacting polyisocyanates with hydroxyalkyl (meth)acrylates with or without chain extenders, such as diols, polyols, diamines, polyamines, dithiols or polythiols. The polyurethane acrylates preferably have a number-average molecular weight from 1000 to 30,000, in particular from 1500 to 20,000 g/mol (determined by gel permeation chromatography using polystyrene as the standard).

The urethane acrylates preferably contain from 1 to 5, with particular preference from 2 to 4, and with very particular preference from 2 to 3, mol of (meth)acrylic groups per 1000 g of urethane acrylate.

The urethane acrylates are preferably synthesized from
a) $C_1$–$C_8$-hydroxyalkyl (meth)acrylates, $C_2$–$C_{15}$-alkanediols and/or -polyols or $C_2$–$C_8$-alkanolamines as chain extenders; they may also include polyesterols or polyetherols as synthesis components; and
b) aliphatic polyisocyanates, such as dicyclohexylmethane 4,4'-diisocyanate, hexamethylene diisocyanate, isophorone diisocyanate, tetramethylene diisocyanate, trimethylhexamethylene diisocyanate, adducts of these isocyanates with polyfunctional alcohols, such as trimethylolpropane, dimerization or trimerization products of the isocyanates, such as biurets or isocyanurates.

Preference is given to aliphatic polyisocyanates, this term being intended to include not only aliphatic but also non-aromatic alicyclic compounds.

Preferred urethane acrylates are aliphatic urethane acrylates, containing aromatic ring systems, if at all, in minor amounts of, for example, less than 5% by weight, based on the urethane acrylates, and with particular preference containing no aromatic ring systems.

The overall amount of the radiation-curable substances is preferably composed as follows:

(i) from 0.1 to 10% of a phenylglyoxylic ester of the formula I and, if desired, from 0.1 to 9.9% of a further photoinitiator or mixture of photoinitiators, so that the overall amount of photoinitiators does not exceed 10%;

(ii) from 20 to 95% of one or more radiation-curable binders, preferably urethane acrylates, as defined above;

(iii) if desired, from 1 to 95% of one or more radiation-curable reactive diluents, which are preferably free from ether groups;

(iv) if desired, from 0.1 to 60% of a pigment or dye, with or without from 0.1 to 10% of dispersant(s);

(v) if desired, from 0.1 to 10% of further additives, such as, for example, levelling assistants, light stabilizers, matting agents, defoamers, slip additives, amines, etc.;

(vi) if desired, from 1 to 50% of solvent(s), in each case in % by weight and based on the overall weight of the radiation-curable substance.

The radiation-curable compounds preferably include few or no aromatic fractions. The amount of aromatic carbon atoms (i.e., carbon atoms that are part of an aromatic ring system) is preferably below 5% by weight, with particular preference below 2% by weight, and with very particular preference below 0.5% by weight, based on the overall amount of the radiation-curable compounds. In particular it is 0%.

Within the compositions, the radiation-curable substances can be present in solvent-free form, as solutions in organic solvents, or as dispersions in water. Solvents and/or water are generally present in an amount of from 10 to 70% by weight, based on the overall weight of the composition.

Preference is given to solvent-free systems, i.e., the radiation-curable compositions are in the form of a powder coating material. With particular preference, said powder coating material has the following composition:

(i) from 0.1 to 10% of a phenylglyoxylic ester of the formula I with or without from 0.1 to 9.9% of a further photoinitiator or mixture of photoinitiators, so that the overall amount of photoinitiators does not exceed 10%;

(ii) from 20 to 95% of one or more radiation-curable binders, preferably a urethane acrylate, as defined above;

(iii) if desired, from 0.1 to 60% of a pigment or dye, with or without from 0.1 to 10% of dispersant(s);

(iv) if desired, from 0.1 to 10% of further additives, such as, for example, levelling assistants, plasticizers, light stabilizers, matting agents, defoamers, slip additives, amines, etc.;

in each case in % by weight and based on the overall weight of the radiation-curable substance.

In addition to photoinitiators and radiation-curable compounds, the radiation-curable compositions may include further constituents, especially inorganic and organic pigments, such as titanium dioxide, zinc oxide, iron oxide, chromium oxide or azo compounds; binders, such as polyacrylates, levelling agents; adhesion promoters; chain extenders; fillers, such as silicates, carbonates or sulfates; dyes; wetting agents; levelling assistants and stabilizers. For applications in the exterior sector, i.e., for coatings directly exposed to daylight, the compositions comprise especially UV absorbers and free-radical scavengers.

UV absorbers convert UV radiation to thermal energy. Examples of UV absorbers which can be used are hydroxybenzophenones, benzotriazoles, cinnamic esters and oxalanilides.

Free-radical scavengers bind free radicals formed intermediately. Examples of free-radical scavengers which can be used are sterically hindered amines, which are known as HALS (hindered amine light stabilizers) and are described, for example, in WO 98/33761.

For exterior applications, the amount of UV absorbers and free-radical scavengers overall is preferably from 0.1 to 5 parts by weight, with particular preference from 0.5 to 4 parts by weight, based on 100 parts by weight of the radiation-curable compounds.

In addition, the radiation-curable compositions may also include compounds which contribute to curing by other chemical reactions. Suitable examples are polyisocyanates, which crosslink with hydroxyl groups or amine groups.

The radiation-curable compositions are suitable as coating materials. A variety of substrates are appropriate, examples being metal, wood, paper, ceramic, glass and plastic. The coatings concerned can be protective or decorative. In particular, the radiation-curable compositions are suitable for use as coating materials that are employed in the exterior sector, i.e., are exposed to daylight. Examples of such applications are exterior coatings of buildings or parts of buildings, road markings, coatings on vehicles, such as automobiles, trucks, rail vehicles and aircraft. The radiation-curable compositions are particularly suitable as a pigment-free topcoat for motor vehicles.

The radiation-curable coating materials can be applied to the target substrates by known methods. Application techniques such as spraying, rolling, knife coating, etc., are particularly appropriate.

Curing can take place by irradiation with light having a wavelength in the range from 200 to 600 nm. Preferably, however, customary commercial UV lamps are used for irradiation.

Powder coating materials are applied to the target substrate in accordance with conventional powder application techniques, such as electrostatic powder spraying or fluidized-bed sintering. In the case of wood as substrate, a conductivity assistant may be applied, for example, before electrostatic spraying. Following the application of the powder coating material to the substrate, heat treatment is performed at a temperature in the range from 60 to 100° C. in order to melt the powder coating material to form a uniform layer. This is followed by curing by irradiation.

The coatings and products produced using the photoinitiators of the formula I display a high level of resistance to the effects of weathering and, in particular, a low yellowing tendency and high stability to hydrolysis. Even the initial yellowing following heat treatment, which is commonplace with the use of powder coating materials, is reduced. Furthermore, it has been found that the glyoxalic esters of the invention can easily be formulated to radiation-curable compositions. In particular, they generally form clear solutions in the compositions, which is not the case with comparable glyoxalic esters.

The examples which follow elucidate the invention without restricting it.

EXAMPLES

Example 1

Preparation of Pentaerythritol Tetraglyoxylate 12.0 g of pentaerythritol, 42.8 g of phenylglyoxylic acid and 0.27 g of sulfuric acid are suspended in 17.8 g of methylcyclohexane and the suspension is heated under reflux. The water of esterification is removed via a separating vessel, so that the esterification reaction is at an end after 8 hours. Distillation of the methylcyclohexane leaves a solid melt (acid number 25 mg KOH/g). The weight loss after 3 hours at 130° C. is 7.3%.

Example 2

Preparation of 1,4-Butanediol Diglycidyl Ether Diglyoxylate 21.4 g of 1,4-butanediol diglycidyl ether (Araldit DY026) are mixed with 30 g of phenylglyoxylic acid in the presence of 0.5 g of tetrabutylammonium bromide. The mixture is cautiously heated to 103° C. and is held at this temperature for 5 hours until the acid number has fallen to 7.2 mg KOH/g. The product is a highly viscous liquid (153.6 Pas). The weight loss after 3 hours at 130° C. is 0.7%.

Example 3

Preparation of 1,4-Bis(phenylglyoxyloxymethyl) cyclohexane 28.84 g of 1,4-bis(hydroxymethyl)cyclohexane, 72.23 g of methyl phenylglyoxylate and 0.82 g of dibutoxydibutyltin are melted over 180° C. in a reaction flask and methanol is distilled off via a column. After virtually all of the theoretical amount of methanol has passed over, the residue is concentrated on a rotary evaporator, the concentrate is digested in ethanol, and the resulting solid is filtered off with suction. The IR and H-NMR spectra correspond to the expected structure. The melting point is 92° C. The weight loss after 3 hours at 130° C. is 0.5%.

Example 4

4 parts of 1,4-cyclohexanedimethanol di(phenylglyoxylate) were dissolved in 96 parts of Laromer LR 8987 (a mixture of hexanediol diacrylate and an aliphatic urethane acrylate) to give a clear solution. Using a box-type coating bar, a glass plate was coated with this formulation so as to form a film having a thickness of 50 µm or 100 µm. This film was subsequently cured in an IST belt exposure unit at 10 m/min under air.

Pendulum attenuation in accordance with DIN 53157 (ISO Norm 1522): 133 sec

Erichsen indentation in accordance with DIN EN ISO 1520: about 5 mm

Pencil hardness: 2H

Example 5 (Comparative)

4 parts of 4,4'-isopropylidenedicyclohexanol di(phenylglyoxylate) [hydrogenated bisphenol-A-di (phenylglyoxylate)] were insoluble in 96 parts of Laromer LR 8987. Therefore, radiation curing was not possible.

4 parts of 1,4-cyclohexanediol di(phenylglyoxylate) did not dissolve completely in 96 parts of Laromer LR 8987. However, the solubility was sufficient to prepare and cure a film as described above.

Pendulum attenuation in accordance with DIN 53157 (ISO Norm 1522): 141 sec

Erichsen indentation in accordance with DIN EN ISO 1520: about 0.6 mm

Pencil hardness: 2H

Example 6 a) Solubility in hexanediol diacrylate (HDDA)

|  | 1% | 2% | 3% | 4% | 5% | 6% | 7% |
|---|---|---|---|---|---|---|---|
| 1,4-Cyclohexanedimethanol di(phenylglyoxylate) | sol | sol | sol | sol | sol | sol | insol |
| 4,4'-Isopropylidenedicyclohexanol di(phenylglyoxylate) | sol | insol | | | | | |
| 1,4-Cyclohexanediol di(phenylglyoxylate) | sol | sol | insol | | | | |

(insol = insoluble, sol = soluble)

b) The solubility of 2% each of 1,4-cyclohexanedimethanol di(phenylglyoxylate) and 4,4'-isopropylidenedicyclohexanol di(phenylglyoxylate) in an aliphatic urethane acrylate was also tested. The 1,4-cyclohexanedimethanol di(phenylglyoxylate) was soluble, whereas the 4,4'-isopropylidenedicyclohexanol di(phenylglyoxylate) was insoluble or did not dissolve completely.

Example 7

A stirred apparatus is charged with 204.2 p (p=parts) of isophorone diisocyanate and 0.3 p of dibutyltin dilaurate and, at 60° C., 91.64 p of hydroxyethyl acrylate, 36.00 p of butanediol and 11.80 p of trimethylolpropane are added.

The temperature rises exothermically to about 110° C. The mixture is subsequently heated to 135° C. and held at this temperature for 10 minutes, and then cooled to about 100° C. 11.00 p of cyclohexanedimethanol diphenylglyoxylate (photoinitiator) are stirred in, the melt is cast onto aluminum foil, the solidified melt is ground, and particles larger than 40 µm are removed by sieving. In a powder booth, the powder is sprayed electrostatically onto metal sheets, rapidly heated to 130° C. under an IR lamp, and exposed to UV at 40 m/min. Cooling results in hard coating films having good solvent resistance (>50 strokes/MEK).

We claim:

1. A phenylglyoxalic ester of the formula I

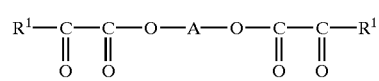

in which $R^1$ is

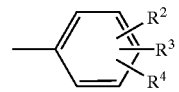

wherein $R^2$, $R^3$ and $R^4$ independently of one another H, $C_1$–$C_6$-alkyl, which is unsubstituted or substituted by OH, $OC_1$–$C_6$-alkyl or $OCOC_1$–$C_6$-alkyl, or are OH or $OC_1$–$C_6$-alkyl;

A is

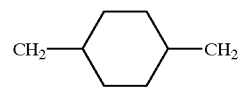

or

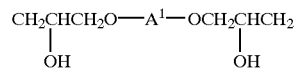

and A¹ is

2. A phenylglyoxalic ester as claimed in claim 1 of the formula I in which $R^2$, $R^3$ and $R^4$ independently of one another are H or $C_1$–$C_6$-alkyl.

3. A radiation-curable composition comprising as photoinitiator at least one phenylglyoxalic ester as claimed in claim 1.

4. A composition as claimed in claim 3 in the form of a powder coating material.

5. A method of coating a substrate comprising:
applying to said substrate a composition as claimed in claim 4;
heat treating the coated substrate to melt the applied composition; and
irradiating the coated substrate with light having a wavelength in the range from 200 to 600 nm.

6. A coated substrate prepared by the method as claimed in claim 5.

7. A coated substrate coated at least partly with a composition as claimed in claim 4.

8. A method of coating a substrate, which comprises applying to said substrate a composition as claimed in claim 3 and irradiating the coated substrate with light having a wavelength in the range from 200 to 600 nm.

9. A coated substrate prepared by the method as claimed in claim 8.

10. A coated substrate coated at least partly with a composition as claimed in claim 3.

11. A method of coating a substrate for exterior applications which comprises applying to said substrate a radiation-curable powder coating material comprising as photoinitiator a phenylglyoxalic ester of formula I

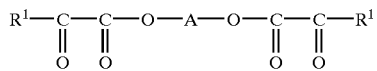

in which the two radicals $R^1$ independently of one another are a radical of the formula

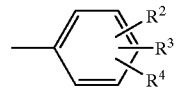

$R^2$, $R^3$ and $R^4$ independently of one another H, $C_1$–$C_6$-alkyl, which is unsubstituted or substituted by OH, $OC_1$–$C_6$-alkyl or $OCOC_1$–$C_6$-alkyl, or are OH or $OC_1$–$C_6$-alkyl;

A is a radical of the formulae

or

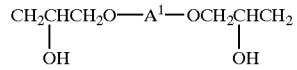

and A¹ is

thereby preparing a coated substrate useful in exterior applications.

12. The method as claimed in claim 11 the exterior coating of buildings or parts of buildings and for coating vehicles or aircraft.

* * * * *